United States Patent [19]

Taboada

[11] 4,453,827

[45] Jun. 12, 1984

[54] OPTICAL DISTORTION ANALYZER SYSTEM

[75] Inventor: John Taboada, San Antonio, Tex.

[73] Assignee: The United States of America as represented by the Secretary of the Air Force, Washington, D.C.

[21] Appl. No.: 297,527

[22] Filed: Aug. 28, 1981

[51] Int. Cl.³ .............................................. G01B 9/02
[52] U.S. Cl. .................................. 356/353; 356/125; 356/127; 356/239; 364/552
[58] Field of Search ............... 356/353, 124, 125, 127, 356/239; 350/314; 364/524, 551, 552, 556

[56] References Cited

U.S. PATENT DOCUMENTS

| | | | |
|---|---|---|---|
| 3,218,916 | 11/1965 | Saunders | 88/14 |
| 3,578,869 | 5/1971 | Irland | 356/239 |
| 3,617,130 | 11/1971 | Kelley | 356/107 |
| 3,652,863 | 3/1972 | Gaskell | 250/219 DF |
| 3,688,235 | 8/1972 | Migotte | 356/239 |
| 3,792,930 | 2/1974 | Obenreder | 356/209 |
| 3,843,890 | 10/1974 | Anthony, Jr. et al. | 250/563 |
| 3,870,415 | 3/1975 | Cornsweet | 356/124 |
| 3,901,596 | 8/1975 | Vincent et al. | 350/314 X |
| 4,007,990 | 2/1977 | McDevitt, Jr. et al. | 356/124 |
| 4,249,823 | 2/1981 | Task | 356/239 X |

OTHER PUBLICATIONS

Wyant et al., "Interferometer for Measuring Power Distribution of Opthalmic Lenses", *Applied Optics*, vol. 14, No. 7, pp. 1607-1611, Jul. 1975.

Balasubramanian et al., "A New Approach to High Precision Phase Measurement Interferometry", *Proc. SPIE*, vol. 230, pp. 180-190, 1980.

Taboada, J. et al., "Shearing Interferometer with Scanned Photodiode Array and Microcomputer for Automatic Transparency Distortion Measurements", *Proc. of the Society of Photo-Optical Inst. Engineers*, Advances in Optical Metrology, vol. 153, 1978, pp. 139-145

*Primary Examiner*—William L. Sikes
*Assistant Examiner*—Matthew W. Koren
*Attorney, Agent, or Firm*—Donald J. Singer; Jacob N. Erlich

[57] ABSTRACT

An optical distortion analyzer system which is capable of automatically quantifying with a high degree of accuracy and repeatability the optical quality of transparencies such as windshields or windows. The analyzer system is made up of a platform adapted to support the transparency with two degrees of freedom. A probe beam of electromagnetic radiation emanating from, for example, a laser is passed through the transparency as the transparency is moved about a horizontal and vertical axis establishing a plurality of test points on the transparency. An analyzer unit receives the probe beam and therefrom establishes horizontal and vertical deviations in the transparency as well as determining the cylindrical and spherical lens power components and principal meridan angle of the transparency. A processor provides recognizable opthalmic parameters of the above characteristics of the transparency and correlates these parameters with the plurality of test points on the transparency.

9 Claims, 10 Drawing Figures

OPTICAL DISTORTION ANALYZER SYSTEM

STATEMENT OF GOVERNMENT INTEREST

The invention described herein may be manufactured and used by or for the Government for governmental purposes without the payment of any royalty thereon.

BACKGROUND OF THE INVENTION

This invention relates generally to optical distortion analyzing systems, and, more particularly to an optical distortion analyzer system which is capable of automatically quantifying with high accuracy and repeatability the optical quality of large area transparencies such as, for example, those found in aircraft windscreens, ground vehicle windshields, windows or the like.

It is often necessary to measure and evaluate the optical quality of large area transparencies used in aircraft, ground transporters, and other windows. The optical quality refers to the manner in which the transparency transmits images without distortion in terms of size, orientation, displacement, deviation and aspect angle of the image. This evaluation is performed for the purposes of quality control in fabrication, selection for use in critical applications, and for feedback into a corrective process such as reforming, polishing, etc.

Current systems utilized in the testing of aircraft transparencies and the like generally do not permit sufficient accuracy to quantify optical imperfections that can be detected by the human eye. Such prior art testing systems usually require photographing a grid pattern through the windscreen or transparency. From the grid photographs, distortion is quantitated as a slope change in the otherwise straight lines of the photographed image. An analysis as presented hereinbelow clearly illustrates the significant limitations of such prior art systems.

More specifically, the camera and windscreen or transparency are treated as a compound lens system where $f_c$=the camera focal length, $f_2$=the local lens power of the distortion of the windscreen, $r$=their separation distance, $f$=the effective system focal length, $p$=the image distance, $g$=the object distance, $x$=the image size, and $y$=the object size. Magnification M, is given by the expression $$M = f/(p-f). \quad (1)$$

Differentiating Equation 1, one obtains the fractional change in magnification given by a fractional change in focal length, f, i.e., $$dM = (p/(p-f)^2)df \quad (2)$$

Let $df = \Delta f = f_c - f_r$, where $f_r$=the focal length of the system with the presence of local distortion anomalie, $f_w$, i.e., $$f_r = f_c f_w/(f_c + f_2 - r) \quad (3)$$

Now $x = My$, where M is the magnification, also $$dx/x = (1/M)dM \quad (4)$$

where $dx/x$=the fractional change in image size. Substituting into Equation 4 the expression for dM of Equation 2, and eliminating df, one obtains an expression for the image size change as a function o the test configuration parameters:

$$dx = y \frac{p}{(p-f_c)^2} \cdot \frac{f_c(f_c - r)}{f_c + f_w - r} \quad (5)$$

A typical numerical example would have g=4.57 m, p=0.09 m, r=1.0 m, y=0.025 m, $f_c$=0.05 m. The human eye can detect imperfections as low as 0.05 diopters in a transparency translated with respect to objects sighted at infinity. Assuming the local distortion on the transparency has a lens effect of 0.05 diopters or $f_w$=1/0.05=20 m, from Equation 5, dx=14 μm. This small spatial change approaches the grain size of some film. Therefore, this level of distortion cannot be conveniently evaluated by such prior art procedures.

A need therefore exists to provide an analyzer system which is capable of accurately and reliably quantifying the optical quality of transparencies. In addition, it would be highly desirable for this sytem to be produced economically.

SUMMARY OF THE INVENTION

The present invention overcomes the problems encountered in the past and as set forth hereinabove by providing a transparency optical distortion analyzer system which is capable of actually quantifying the optical quality of the transparency in terms of well-known opthalmic parameters and to render this information with an unpresidented degree of accuracy and repeatablity. This is accomplished by representing the large area transparency as a large scale opthalmic lens which can then be taken into account or neutralized by process or selection.

It is therefore an object of this invention to provide an optical distortion analyzer system for measuring the optical quality of large area transparencies and to relate this measurement in terms of a map of well known opthalmic parameters.

It is another object of this invention to provide a transparency optical distortion analyzer system which automatically compensates for the misalignment of a probe beam due to prismatic deviation or displacement as it passes through the transparency.

It is a further object of this invention to provide a transparency optical distortion analyzer system which is capable of automatically measuring, computing and mapping the horizontal and vertical prismatic deviations throughout the transparency under examination.

It is still a further object of this invention to provide a transparency optical distortion analyzer system which is capable of compensating the effect of multiple reflections that occur when thick transparencies are scanned at large angles to normal incidence.

It is still another object of this invention to provide a transparency optical distortion analyzer system for performing highly sensitive, accurate and automatic measurement, computation and mapping of the cylindrical lens power component of the test point.

It is still another object of this invention to provide a transparency optical distortion analyzer system for performing highly sensitive, accurate and automatic measurement, computation and mapping of the spherical lens power component and sign of the test point.

It is still a further object of this invention to provide a transparency optical distortion analyzer system which is capable of automatically compensating for optical modification caused by translation of the test point along the test region axis as in the case of highly slanted gimballed transparencies.

It is still another object of this invention to provide a transparency optical distortion analyzer system which automatically compensates for local transmissivity variations throughout the transparency under test.

It is still another object of this invention to provide a transparency optical distortion analyzer system which is capable of being calibrated in a highly accurate and reproducible manner and achieving a highly stable measurement.

It is still a further object of this invention to provide a transparency optical distortion analyzer system which is economical to produce and which utilizes conventional, currently available components that lend themselves to standard mass producing manufacturing techniques.

For a better understanding of the present invention, together with other and further objects thereof, reference is made to the following description taken in conjunction with the accompanying drawings and its scope will be pointed out in the appended claims.

DETAILED DESCRIPTION OF THE DRAWING

DETAILED DESCRIPTION OF THE PREFERRED EMBODIMENT

Figure 1:
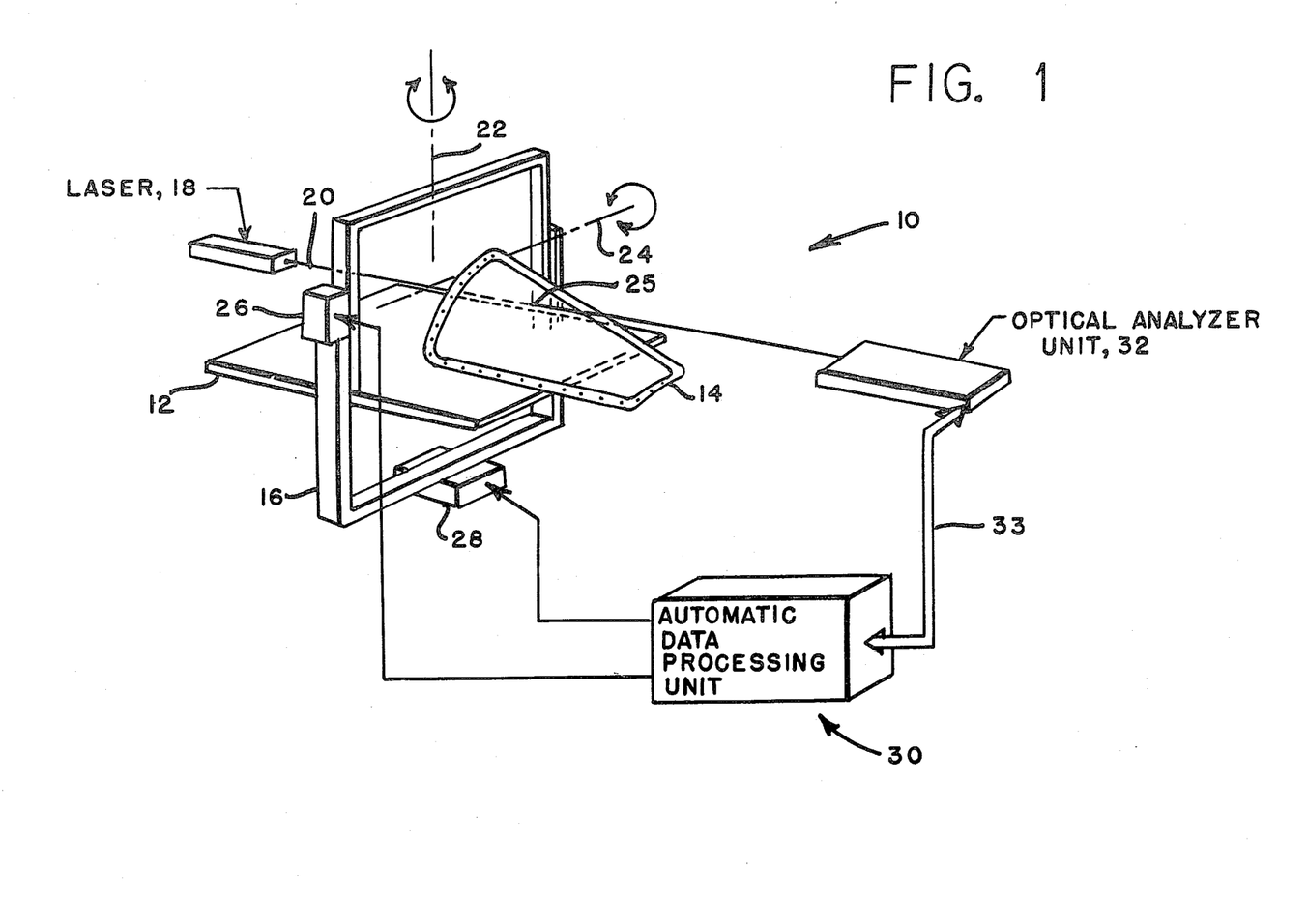
FIG. 1 is a pictorial representation of the transparency optical distortion analyzer system of this invention.

Reference is now made to FIG. 1 of the drawing which illustrates in pictorial fashion the main components of the transparency optical distortion analyzer system 10 of this invention. Analyzer 10 incorporates therein a platform 12 upon which any suitable transparency 14 such as a windscreen or window may be placed while undergoing testing by the analyzer system 10 of this invention. Platform 12 is connected in any suitable manner to a support frame 16 which is capable of two degrees of freedom of movement, that is, about the horizontal and vertical axes. The actual operation of support frame 16 will be set forth in detail hereinbelow.

Still referring to FIG. 1 of the drawing any suitable source of electromagnetic radiation in the form of, for example, a laser 18 is positioned in operative relationship with platform 12 and frame 16 as well as in optical alignment with the transparency or windscreen 14 to be tested. Laser 18 can be any conventional low power laser such as, for example, a HeNe laser manufactured by Spectra Physics as Model 124B. Its power output may be in the range of 15 mW.

Laser 18 produces a probe beam of electromagnetic radiation 20 which is so situated with respect to transparency 14 that it passes through the transparency 14 undergoing analysis. For purposes of illustration, an aircraft windscreen 14 is utilized with this invention and is shown gimballed about the vertical and horizontal axes 22 and 24, respectively, by frame 16. The center of intersection of the gimbal axis is at the design eye position for a pilot utilizing the windscreen. The test point 25 where laser probe beam 20 intersects windscreen 14 is mapped throughout the entire clear aperture by motion generated by elevation and azimuth gimbal drives 26 and 28, respectively, thereby establishing a plurality of test points 25 throughout the transparency. The gimbal drives 26 and 28 are under the control of a conventional automatic data processing unit 30 in the form of, for example, a medium frame computer such as manufactured by Digital Equipment Corporation as Model 11/34. Data processing unit 30 will have its operation more fully described hereinbelow.

Probe beam 20 having passed through windscreen 14 is received by, tracked and analyzed by an optical anlyzer unit 32 described in more detail hereinbelow with respect to FIGS. 2 and 3 of the drawing. The data signals 33 generated by analyzer unit 32 are transmitted to the automatic data processing unit 30.

Figure 2:
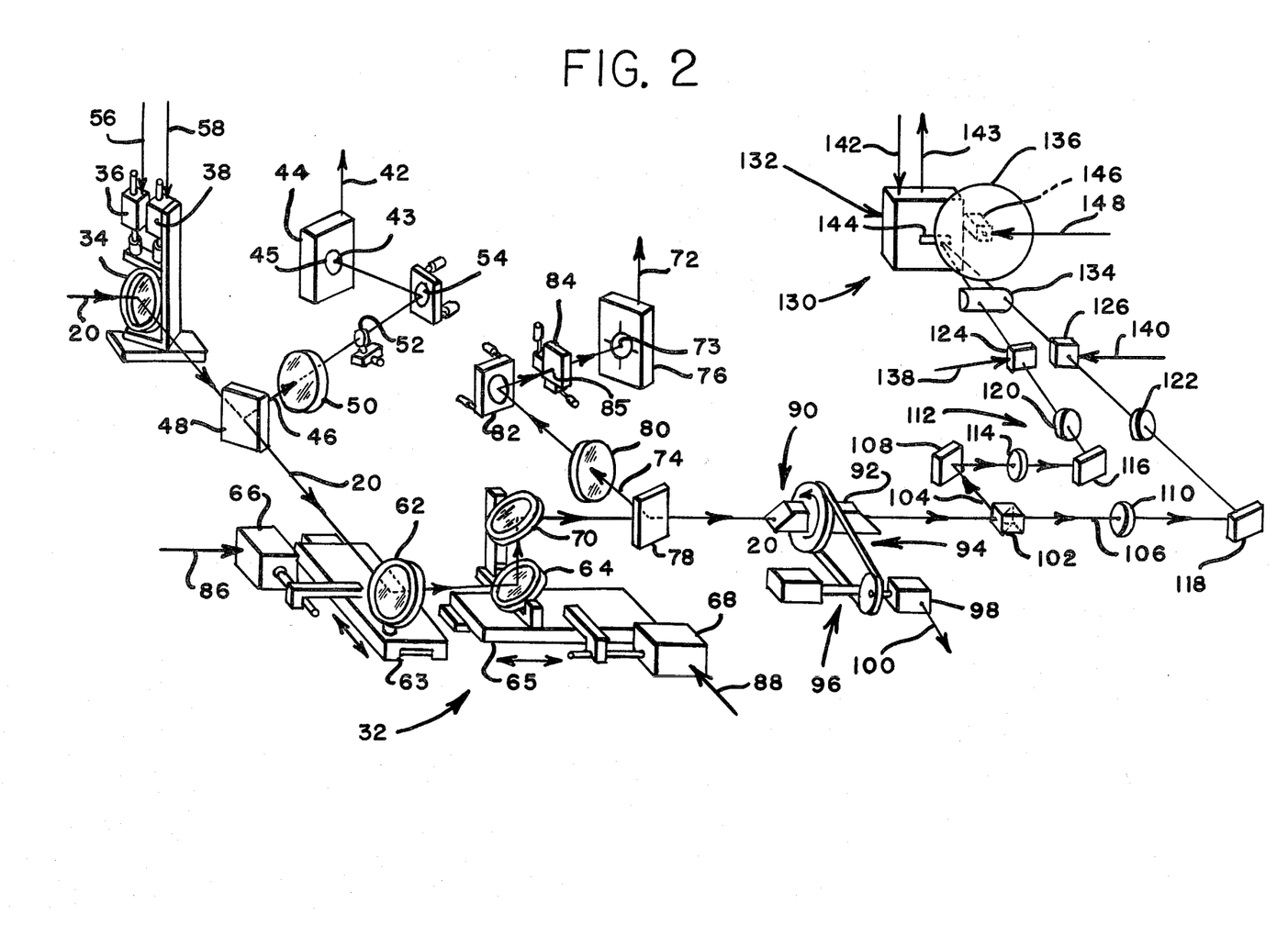
FIG. 2 is a schematic, pictorial representation of the components of the optical analyzer unit of the transparency optical distortion analyzer system of this invention.
Figure 3:
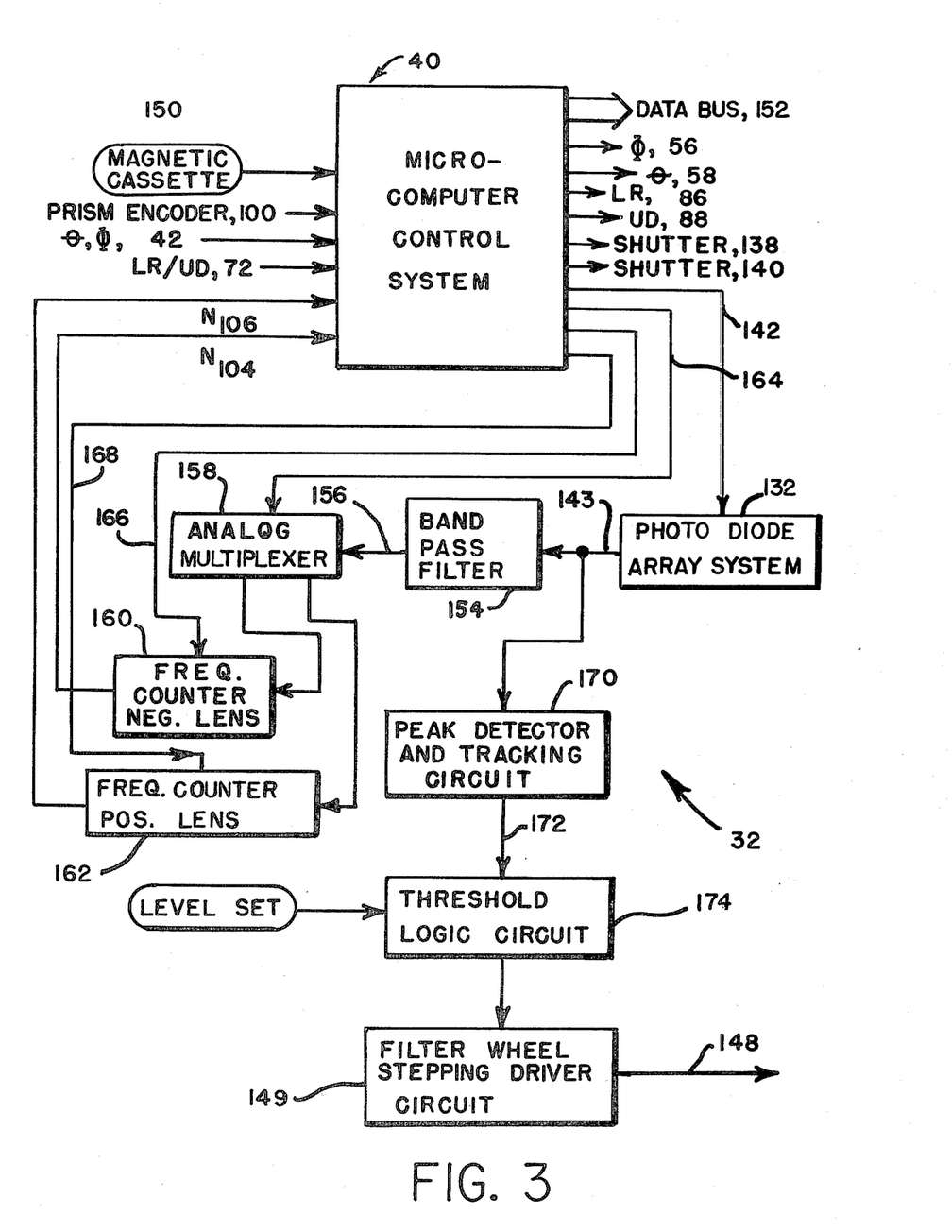
FIG. 3 is a schematic diagram of the electronic components of the optical analyzer unit of the transparency optical distortion analyzer system of this invention.

Reference is now made to FIGS. 2 and 3 of the drawing which more specifically set forth in detail the optical and electronic components of analyzer unit 32. As shown in FIG. 1 of the drawing probe beam 20 after having passed through a given test point 25 on windscreen 14 is received by a gimballed reflecting element in the form of mirror 34 (shown in FIG. 2 of the drawing) driven by conventional azimuth and elevation stepping motor drivers 36 and 38. These stepping motors 36 and 38 can be obtained, for example, from Aerotech Incorporated as Model 200-1 with driver electronics. The purpose of the gimballed mirror 34 is to restore probe beam 20 to its original angular orientation (null) so as to permit the measurement of the prismatic deviation by counting the steps required to restore the probe beam to its null position. This information is obtained from a feedback control loop using a conventional electronic control system 40 illustrated in FIG. 3 of the drawing which contains therein any suitable microcomputer such as produced by MOS Technology Inc. as model KIM-1.

More specifically, an error signal 42 is generated by the displacement of the sampled beam spot 43 incident on a conventional quadrant detector 44 such as a United Detector Technology PIM spot/9D. The quadrant detector 44 has a sensor surface 45 which is at the focus of a sample beam 46 of the probe beam 20 obtained from beam splitter 48, a pair of focusing lenses 50 and 52 and a mirror 54. Lens 52 is translatable to allow precision focus while mirror 54 which is adjustable is used to align the focus beam spot at null. Since the spot 43 of the sampled beam 46 is at the focus of a lens it is capable of being used to only detect deviation. The error signal 42 is converted by the electronic control system 40 of FIG. 3 into direction and step command signals 56 and 58 for each angular coordinate $\phi$ and $\theta$, respectively. The above mentioned assembly of elements therefore form part of this invention capable of automatic measurement, computation and mapping of the horizontal and vertical prismatic deviations throughout the transparency 14 under examination.

As clearly illustrated in FIG. 2 of the drawing the main probe beam 20 continues through beam splitter 48 to a pair of translatable reflecting elements in the form of mirrors 62 and 64 on movable mounts 63 and 65, respectively, whose position along the perpendicular directions is controlled by conventional stepping motor drivers 66 and 68, respectively of the type described hereinabove. The purpose of the translatable mirror pair 62 and 64 when taken in conjunction with a stationary mirror 70 is to restore the probe beam 20 to its original (colinearity) paraxial juxtaposition, that is, probe beam 20 is positioned parallel to and superimposed with the original beam direction and position is space. This function is obtained by a feedback control loop using the electronic control system 40 of FIG. 3.

An error signal 72 is generated by the displacement of a spot 73 from a sampled beam 74 which is incident upon a conventional dual axis beam position sensor 76 such as a United Detector Technology PIN-SC/50. Position sensor 76 is in an unfocused region of the sampled beam 74 obtained from beam splitter 78 after passing through conventional focusing optics in the form of lens 80, a precision adjustable mirror 82 and a pinhole aperture plate 84 through which it passes. The pinhole 85 in aperture plate 84 compensates for the effect of multiple reflections that occur when thick transparencies are scanned at large angles to normal incidence. The optical path distance from lens 80 (a positive lens) reflecting off mirror 82 to aperture plate 84 is equal to the focal length of lens 80.

As stated above aperture 85 within aperture plate 84 screens out the spurious multiple images or reflections occuring when probe beam 20 undergoes partial reflections on thick transparencies oriented at acute angles. The spurious angles would otherwise cause alignment errors. The position sensor 76 is located beyond the focal plane of lens 80, therefore, it will sense displacement as well as deviation. The deviation, however, is corrected by the gimballed mirror 34 set forth hereinabove. The error signal 72 is converted by the electronic control system 40 into direction and step commands or signals 86 and 88, for the horizontal and vertical displacement correctors in the form of stepping motor drivers 66 and 68, respectively.

Referring once again to FIG. 2 of the drawing, the main probe beam 20 after passing through beam splitter 78 passes to a conventional image plane rotator 90 made up of, for example, a dove prism 92 and a belt drive 94 which is coupled to a motor 96 and an optical shaft encoder 98. The output 100 of the shaft encoder 98 is transferred to the electronic system 40 for subsequent data output. The purpose of the image plane rotator 90 is to permit rotation of the image axis of the probe beam 20 and thus allow a measurement of the cylindrical lens power and principal meridian angle in a manner to be set forth in more detail hereinbelow.

Thereafter the rotating probe beam 20 passes to a beam splitter cube 102 which generates two equal intensity beam samples 104 and 106. Sample beam 104 is reflected off a conventional reflecting element in the form of mirror 108 while sample beam 106 is directed into a lens 110. Sample beams 104 and 106 are then analyzed by a novel dual channel differential shearing interferometer 112. The dual interferometer 112 is made up of previously refered to beam splitter cube 102 and mirror 108, a pair of bias lenses in the form of lens 114 and the heretofore referred to lens 110, shearing plates 116 and 118, back correcting lenses 120 and 122 and sequencing shutters 124 and 126 and a cylindrical lens 134. The power of one of the biasing lenses 114, for example, is negative while the other biasing lens 110 is positive. The corresponding lenses 120 and 122, respectively, are of opposite signs and of comparable magnitude.

The function of the interferometric arms containing either beam 104 or 106 can be understood by compounding the lens power of the point 25 under test on windscreen 14 (along the given shear direction defined by rotator 90 and shearing plates 116 and 118) with the lens power of the bias lenses 114 or 110. If the maximum effective lens power excursion on windscreen 14 at test point 25 is assumed to be $\pm |F_1|$, then the required lens powers are such that if $F_2$ and $F_3$ are the lens powers of the bias lenses 114 and 110, respectively, and then the required values satisfy the conditions, $$F_2 > |F_1| \qquad F_3 < - |F_1| \qquad (1)$$
$$F_2 < O \qquad F_3 < O.$$

The effective lens power of the compounded systems in the respective arms containing beams 104 or 106 will be given by $$F_{104} = F_1 + F_2 - r F_1 F_2 \qquad (2)$$

$$F_{106} = F_1 + F_3 - r F_1 F_3$$

where $F_{104}$ and $F_{106}$ are the effective lens powers after lenses 114 and 110 respectively, and r is the distance from test point 25 on windscreen 14 to lenses 114 and 110. The conditions set forth in the equation (1) assure that the resultant effective lens power does not go through zero; thus lenses 114 and 110 function as bias lenses.

It is generally recognized that a beam of coherent laser light passing through a lens and incident on a shearing plate will generate a set of interference fringes whose number is directly related to the lens power and the beam diameter. This was shown by the inventor, J. Taboada, and B. R. Altschuler in a technical article entitled "Rectangular Grid Fringe Pattern for Topographic Applications", *Applied Optics* 15, (1976), pp 597-599. For a beam of diameter $w_o$ and wavelength $\lambda$, decollimated by a lens of focal length $f_o$ and incident at an angle $\theta$ from the normal on a shearing plate of thickness l and index of refraction n, the number of fringes is given by the equation:

$$N = \left( \frac{\sin 2\theta}{\sqrt{n^2 - \sin^2\theta}} \right) \frac{2l}{\lambda} \tan^{-1}(w_o/2f_o). \qquad (3)$$

For typical values: $\theta=30°$ and $n=1.5$, the quantity in the first parenthesis is approximately 0.61 and the expression for fringe number is then $$N=(1.22 \, l/\lambda) \tan^{-1}(w_o/2f_o). \quad (4)$$

Solving for the lens power $F_o$ as determined by the number of fringes, one obtains $$F_o=1/f_o=(2/w_o) \tan (N\lambda/1.22 \, l) \quad (5)$$

Since $N\lambda/1.22 \, l << 1$, $$F_o=(2/w_o)(N\lambda/1.22 \, l) \quad (6)$$

By the above equations, a straight forward linear relation is obtained between the total lens power in the test region (plus the bias lens in a given interferometer arm) and the number of fringes in the output direction of the given shearing plates. Calibration of this relation is readily accomplished by inserting, instead of windscreen 14, standard lenses which have magnitudes satisfying the conditions of inequality set forth in equation (1).

The differential property of the dual shearing interferometer 112 is employed to eliminate the lens power error caused by translation of the test point 25 along the optical axis, i.e., variations with r in equation (2). Through calibrations of the form given in equation (6), the lens power in each arm $F_{104}$ and $F_{106}$ are determined. Computing the sum $F_{104}+F_{106}$ from equation (2) gives $$F_{104}+F_{106}=2F_1+F_2+F_3-rF_1F_2-rF_1F_3. \quad (7)$$

Now, if the magnitude of the bias lenses 114 and 110 are chosen such that $F_2=-F_3$, then from equation (7), $$F_{104}+F_{106}=2F_1, \quad (8)$$

and the tranlational artifact is effectively eliminated. The lens power in the direction of shearing is then given as the mean of the determinations obtained through the negatively and positively biased systems. Stated more succinctly, the dual shearing interferometer 112 automatically compensates for optical modifications (as explained in the results of equation (8)) caused by translation or displacement of test point 25 along the test region axis as in the case of highly slanted gimballed transparencies.

The remaining component of the optical analyzer unit 32 of the optical distortion analyzer system 10 of this invention is in the form of a multiplexed fringe detection and counting arrangement 130. The multiplexed fringe detection and counting arrangement 130 is designed to achieve fractional fringe resolution. This is accomplished by an optimum removal of fringe member ambiguity caused by non-unity fringe contrast and by compensating fringe pattern intensity variation caused by transmissivity changes on the windscreen 14. Multiplexing reduces the complexity and cost of system 10 and increases the reliability and speed of data acquisition.

Fringe detection and counting arrangement 130 optically follows shearing interferometer 112. Its operation basically involves two fringe patterns being projected onto a conventional single line image scanner or photodiode array system 132 in the form of, for example, a Reticon RL-512 EC. The fringe beams 104 and 106 pass through back-correcting lenses 120 and 122, programmable shutters 124 and 126, cylindrical lens 134 and a variable density filter wheel 136. The function of programmable shutters 124 and 126 is to pass their respective fringe patterns only on command from the electronic system 40 shown in FIG. 3 of the drawing through input signal lines 138 and 140. This operation synchronizes the data scan of the photodiode array system 132 with the appearance of a given fringe pattern for the acquisition of the fringe count number in separate scalers as shown in FIG. 3. Conventional electro-optic shutters 124 and 126 such as Kerr cells or Pockels cells can be used for this purpose as well as any number of mechanical devices such as rotary light choppers. A reference for such devices is set forth in "Optics" by Hecht and Zajac, Addison Wesley, New York, Pgs 264 and 265. The fringe scanner or photodiode array system 132 is controlled through signal 142 from electronic control system 40.

The cylindrical lens 134 focuses the vertically distributed radiation of the fringe patterns onto the diode array elements 144 of photodiode array system 132 while the fringe contrast remains undisturbed. Controlling the fringe pattern intensity maintains the fractional resolution of the system through large transmissivity variations of the windscreen test sample 14. This control is accomplished by the variable density filter wheel 136 driven by a conventional stepping motor 146. The angular orientation of the filter wheel 136 is determined by direction and step signals 148 from the filter wheel stepping driver circuit 149 which is available, for example, from Aerotech, Inc. as Model 200-1. These signals are generated as the output of an intensity controlling feedback loop of the type, for example, utilized in U.S. patent application Ser. No. 297,526 entitled Optical Beam Intensity Control System by this inventor and filed on Aug. 28, 1981 using the magnitude of the peak video signal from array system 132 compared to a presettable internal reference set forth in FIG. 3 of the drawing.

Figure 4:
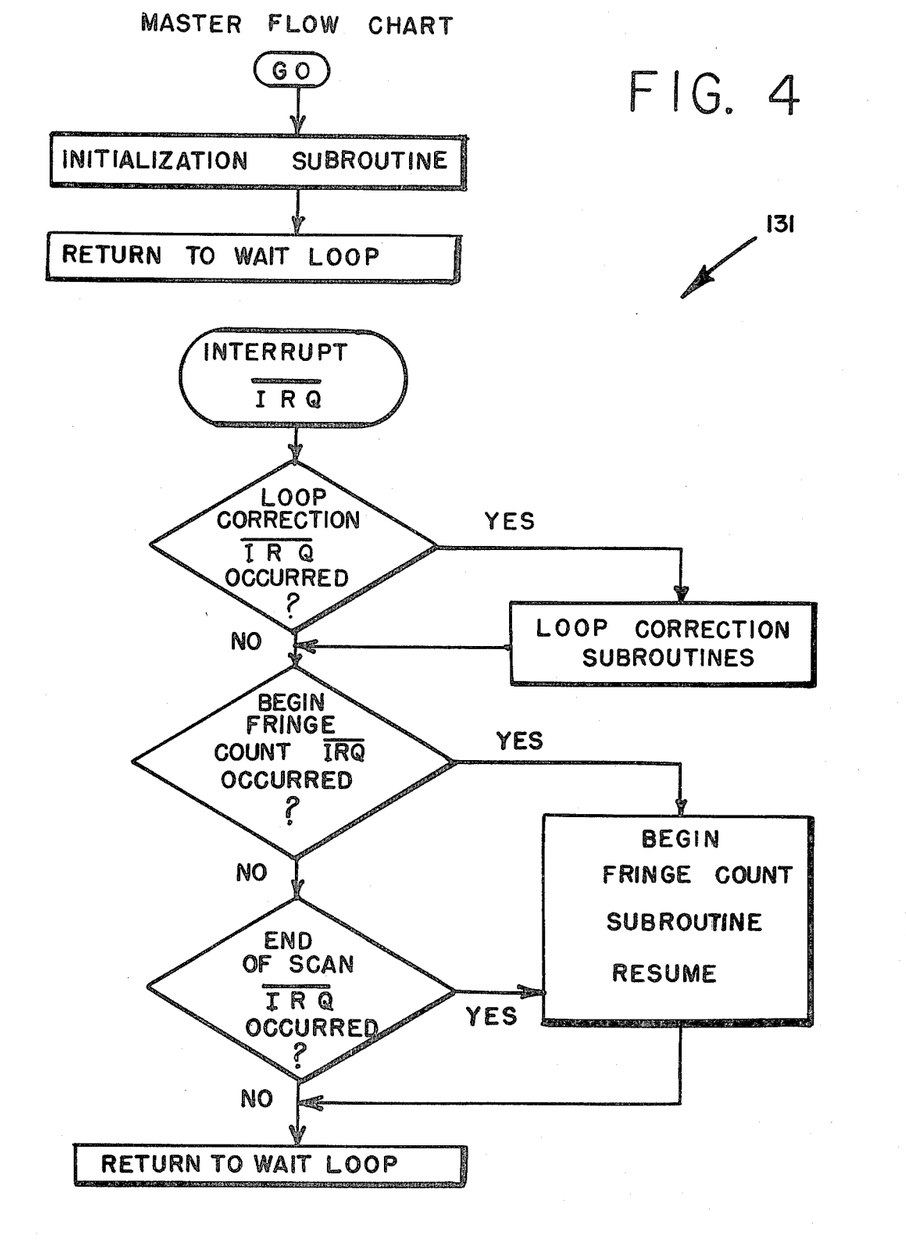
FIG. 4 is a schematic diagram of the master flow chart utilized with the microcomputer of the optical analyzer unit of the transparency optical distortion analyzer system of this invention.
Figure 5:
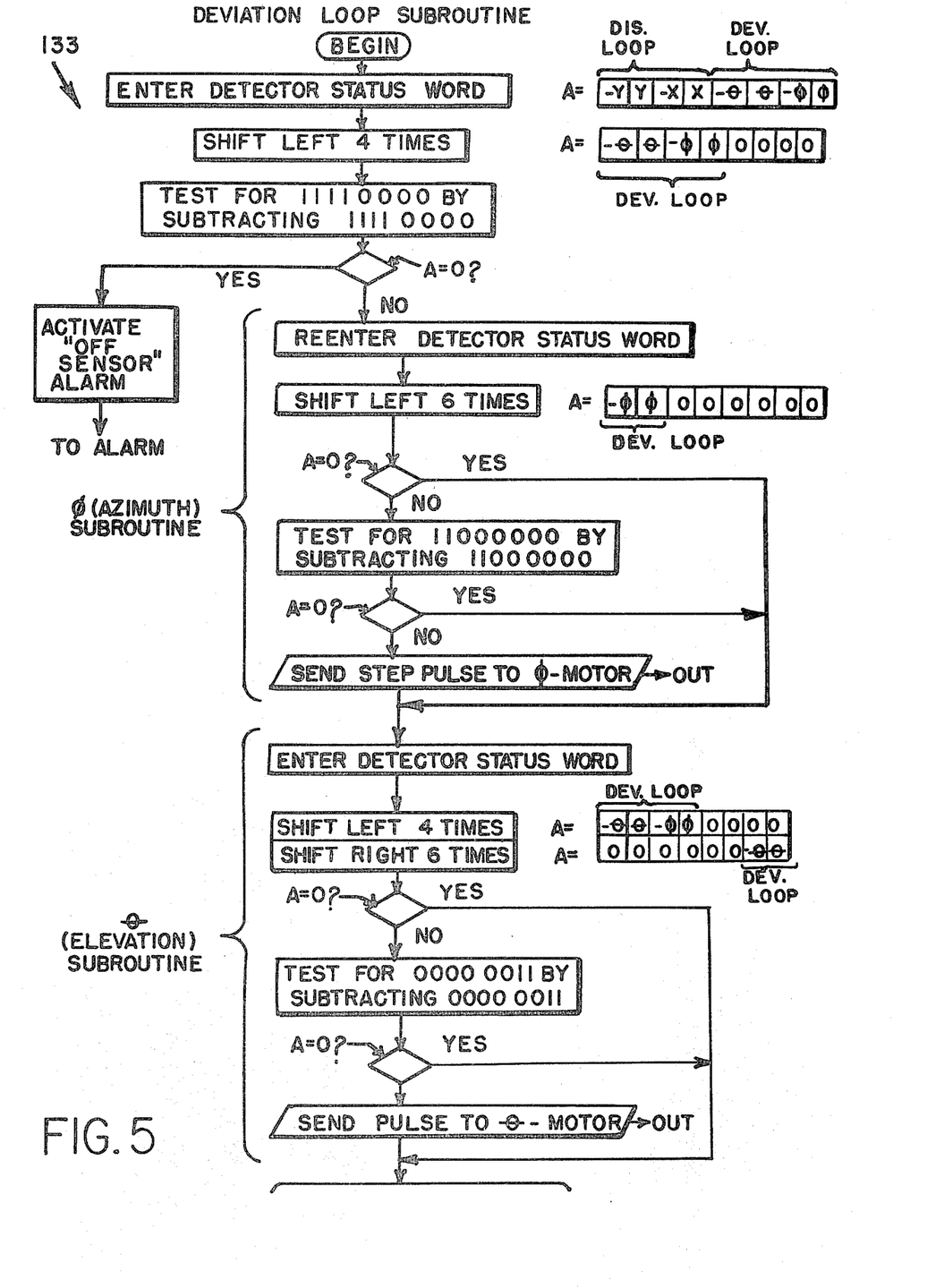
FIG. 5 is a schematic diagram of the deviation loop subroutine utilized with the microcomputer of the optical analyzer unit of the transparency optical distortion analyzer system of this invention.
Figure 6:
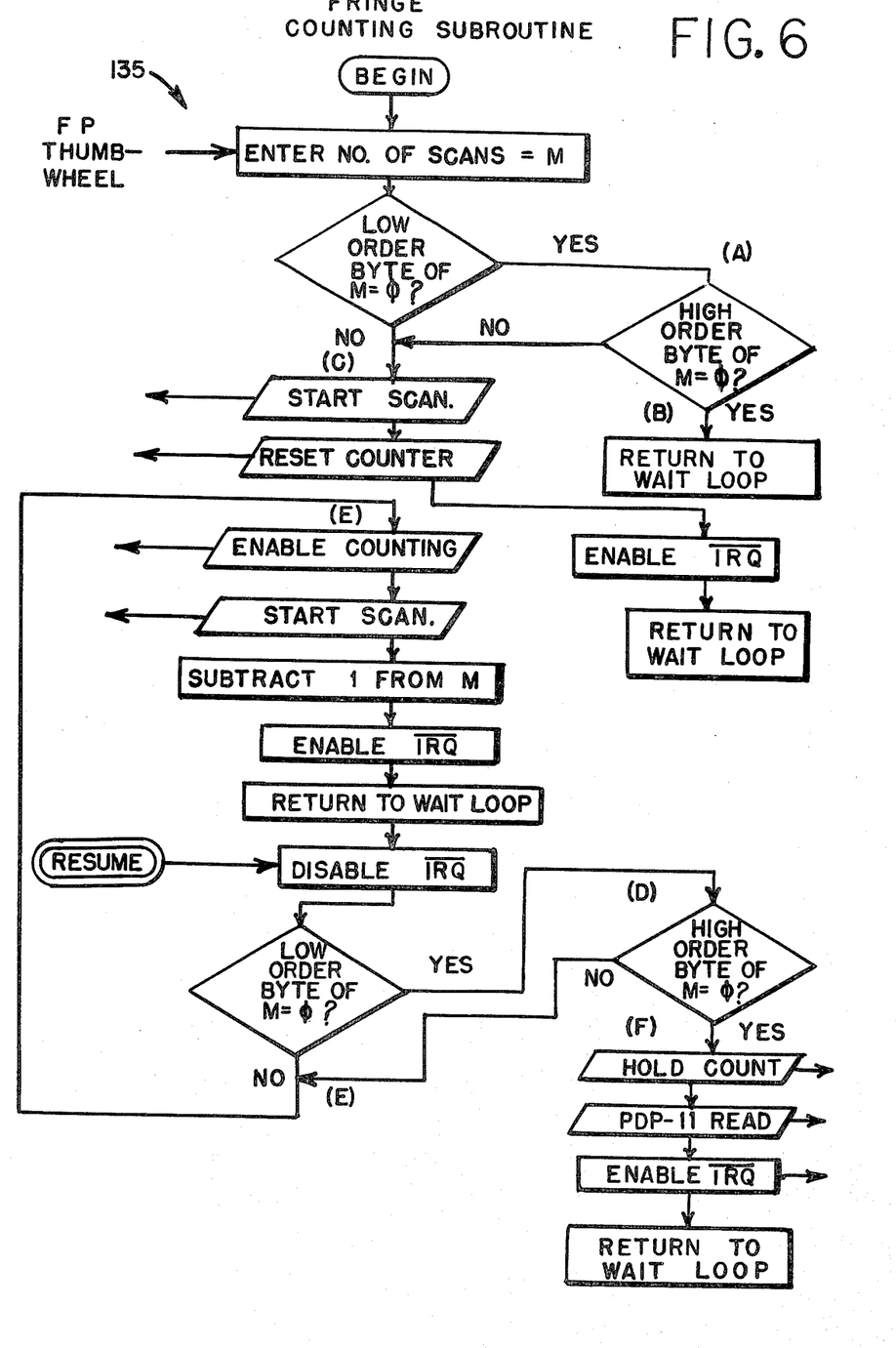
FIG. 6 is a schematic diagram of the fringe counting subroutine utilized with the microcomputer of the optical analyzer unit of the transparency optical distortion analyzer system of this invention.
Figure 7:
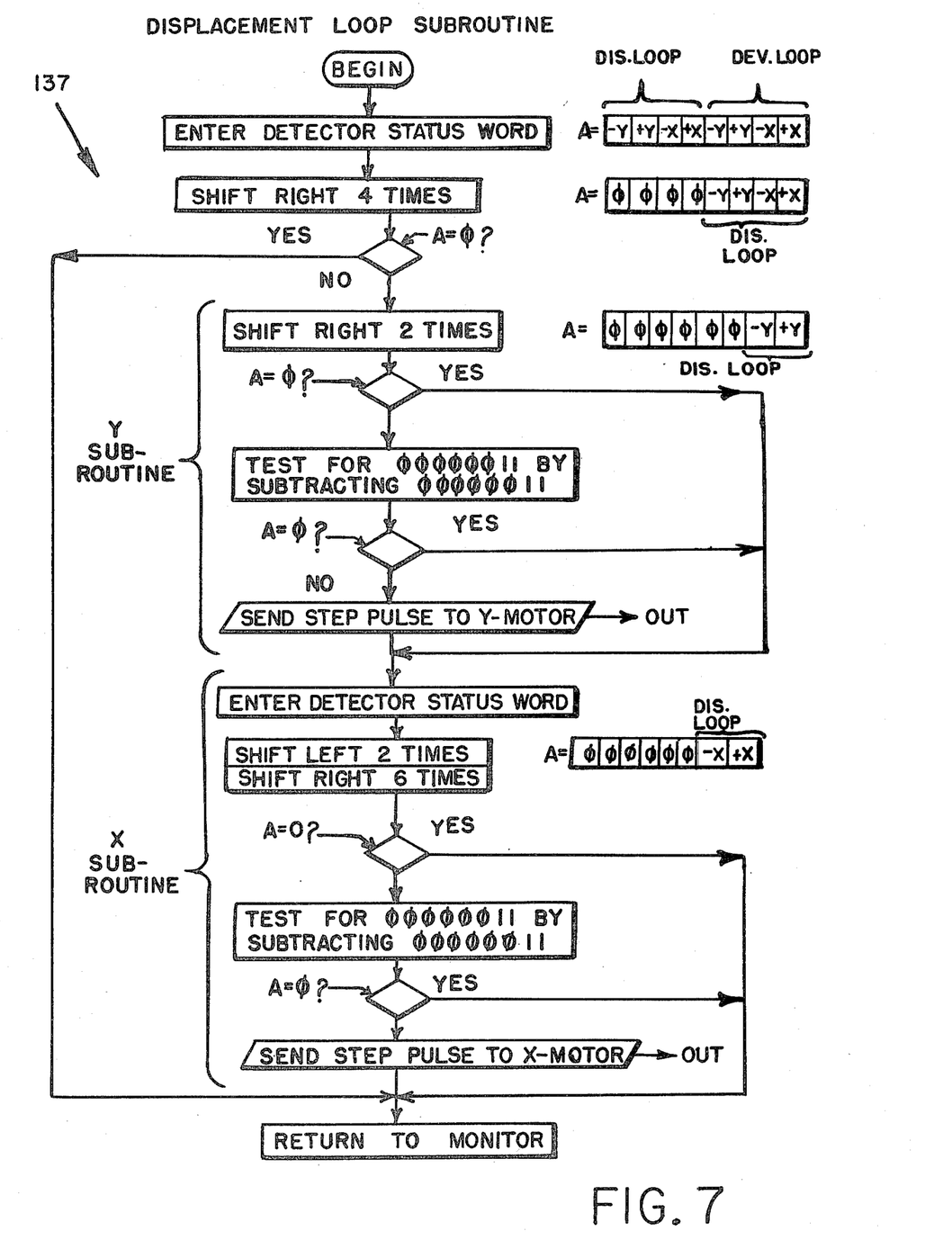
FIG. 7 is a schematic diagram of the displacement loop subroutine utilized with the microcomputer of the optical analyzer of the transparency optical distortion analyzer system of this invention.

Reference is now made to FIG. 3 of the drawing for more specific details of the electronic control system 40 of optical analyzer unit 32 utilized with this invention. Electronic control system 40 controls the electromechanical components set forth in details hereinabove of the optical analyzer unit 32 and conditions signals and data from the combined systems for transfer to the automatic data processing unit 30. As stated hereinabove, the electronic system 40 is basically in the form of an interruptable microcomputer which may be manufactured by MOS Technology Incorporated as Model KIM-1 with appropriate hardware interfaces and control software. Inputs are on the left while outputs are on the right. The microcomputer under the control of an appropriate program based upon a master flow chart 131 shown in FIG. 4 of the drawing, a deviation loop subroutine 133 shown in FIG. 5 of the drawing, a fringe counting subroutine 135 shown in FIG. 6 of the drawing, and a displacement loop subroutine 137 shown in FIG. 7 of the drawing. The microcomputer of control system 40 therefore performs the logical operations on the error signals to generate the corrective feedback output commands. The microcomputer also performs a synchronization of the photodiode array system 132 (for fringe image line scans) with the programmable shutters 124 and 126.

More specifically, the electronic control system 40 is programmed by a conventional magnetic cassette 150.

The system conducts the housekeeping chore of keeping the probe beam 20 on target and in coaxial juxtaposition with the original alignment prior to the insertion of windscreen 14. This is done by acquiring error signals 42 from the quandrant detector 44 for azimuth and elevation deviation departures ($\theta,\phi$) and error signals 72 from the positive sensor 76 for left-right and up-down (LR/UD) displacement departures. These error signals 42 and 72 are converted by a logical operation to corrective commands to the mirror stepping motors 36, 38, 66, and 68 as illustrated in FIG. 2 of the drawing by means of input signals 56, 58, 86 and 88. The size and magnitude of the prismatic error (the number of steps required to achieve null) is the prismatic deviation and it is put onto a conventional data bus 152 for data retrieval purposes.

The shaft encoder signal 100 from the prism rotator 98 is used for the synchronization of the lens power sampling as a function of angle. This signal 100 is also put on data bus 152 for correlation of the lens power with shear plane angle, a process that gives the cylinder power and axis as will be shown hereinbelow.

The photodiode array system 132 also illustrated in FIG. 2 is controlled by a signal 142 from the microcomputer, signal 142 being based on the prism encoder angle signal 100. The output 143 of the photodiode array system 132 is a repetitive signal of intensity versus time where time is the converted spatial variable. Signal 143 has a pedestal and does not lend itself to the counting of the fringe peaks. To improve signal 143, a conventional bandpass filter 154 is adjusted to pass only the "spatial" frequency of the fringes. As the fringes have roughly constant spatial frequency, bandpass filter 154 can be narrowly set and only fringe produced oscillations are passed as signal 156.

A conventional analog multiplexer 158 which can be obtained from Datel Systems, Inc., for example, as Model MM 16 is synchronized with the photodiode array system 132 and shutter control signals 138 and 140 which are all synchronized with the prism encoder signal 100. Analog multiplexer 158 transfers the fringe pattern signal 156 to conventional frequency counters 160 and 162. Control line 164 accomplishes the multiplexing control so that the fringe pattern signal 156 is scaled in the negative lens frequency counter 160 when shutter 124 is opened and shutter 126 is closed. The fringe pattern is scaled in counter 162 for the opposite condition. Frequency counters 160 and 162 have Schmidt triggering inputs and their thresholds are set at zero. This reduces the noise and non-fringe count errors.

Counters 160 and 162 are reset by signals 166 and 168 from the microcomputer of control system 40. The fringe counts in the given counters $N_{104}$ and $N_{106}$ accumulated over several scans represent the lens power as sensed by the negative biased interferometer and by the positive interferometer, respectively. As several scans can be made by the photodiode array system 132 in a very short time interval, reasonable statistically stable numbers are recorded. These numbers are also placed on data bus 152 for retrieval and subsequent conversion to lens power at a given angle of the shear in the image plane. The summation of the determinations (as was shown above) by the two channels of the multiplexed dual shearing interferometer 112 eliminates the longitudinal displacement error.

Further control for optimum independence of the lens power measurement from transmissivity artifacts is achieved by the intensity controller, the variable density wheel 136 driven by stepping motor 146. The control signal 148 in this feedback loop is generated from a sample signal of the fringe pattern intensity versus time signal 143. This signal is passed through a conventional peak detector and tracking circuit 170. An example of such a circuit can be found in a book by H. M. Berlin entitled "Design of OP-AMP Circuits", Howard Sams Publ., Indiana, 1978, pgs. 113, 114. The peak signal 172 is held and reestablished from scan to scan and represents the peak fringe intensity. As the Schmidt thresholds in the counters 160 and 162 are set around zero, controlling the intensity assures the maintainence of a high fringe signal-to-noise ratio. A conventional threshold logic circuit 174 with manually set levels responds to excursions going beyond the levels and commands the filter wheel driver circuit 149 to restore the preset intensity. The driver circuit 149 by signal 148 directs the stepping motor 146 in direction and step number to increase or decrease the optical density necessary to restore the preset value of transmitted intensity. The variation in intensity due to the angle of the windscreen changes are thus conveniently compensated.

In summary, at every presettable integer fraction of 360° of rotation (e.g., 15°, 30°, 45° etc) of prism shearing plane rotator 90, the microcomputer presents on data bus 152 the following information:

(1) the encoded angle (as rotated by prism 92) that the direction of shearing plane of the interferometers make with a given axis such as vertical or horizontal;

(2) the prismatic deviation error count for azimuth or elevation angles;

(3) the fringe pattern count for the negative bias lens interferometers; and (4) the fringe pattern count for the positive bias lens interferometers.

Throughout the operation, control system 40 maintains probe beam 20 locked on its original direction and position with constant peak intensity at the photo diode array system 132. For the purpose of calibration and acquisition, the data is processed at the automatic data processing unit 30, as described hereinabove would preferably be in the form of a conventional medium frame computer. The theory and practice of how this information is processed into well known ophthalmic parameters will be discussed next.

Figure 8:
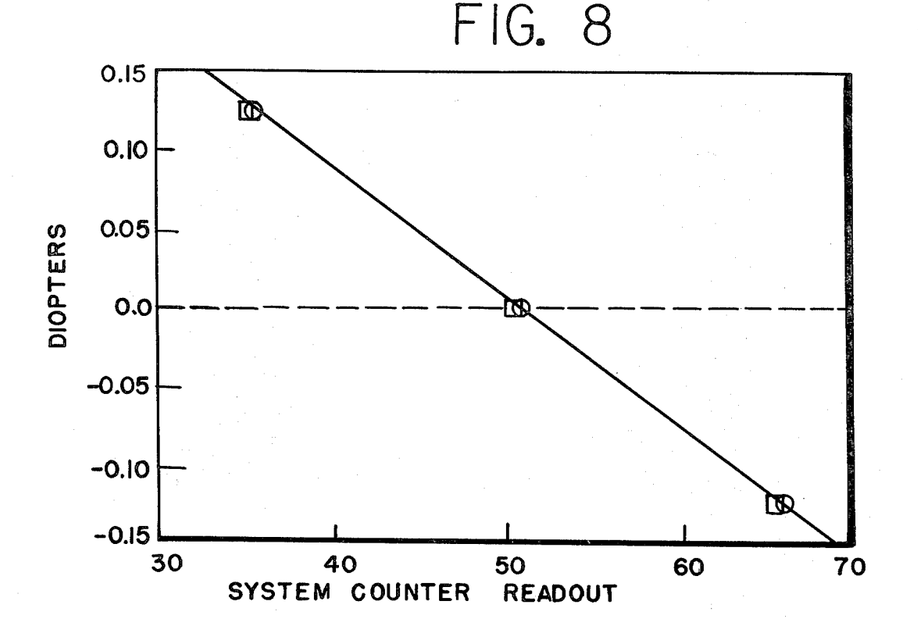
FIG. 8 is a graphic representation of a system calibration curve based on standard lenses.

To obtain calibration of the analyzer system 10, spherical lenses of calibrated and certified precision and power values are placed in the test regions where windscreen 14 is to be scanned. FIG. 8 shows typical results for the output of the entire system for several test lenses. These results can be simply expressed as the linear regression equation $$D=0.4179-(8.274\times 10^{-3})R, \qquad (9)$$

where D is the lens power measurement in diopters and R is the fringe counter readout. This calibration results is for a negative bias lens interferometer. A similar result would be obtained for the positive bias lens interferometer, however, the slope would be positive. The lens power measurement for the two interferometers are arranged as discussed above to eliminate dependence on testpoint-to-optical analyzer distance. Since spherical lenses have radial symmetry, all the readings in a 360° rotation of the shearing plane can be averaged to derive the responsivity calibration relation of equation (9). To obtain the measurement of cylindrical lens parameters in the test region, use is made of the angular sampling capability provided by the rotation of the shearing plane with the dove prism 92.

An optical assembly that can be used to calibrate the cylindrical lens response of analyzer system 10 of this invention can be readily produced. Two spherical lenses, one of power S and the other of power U are used. The lens of power U is aligned normal to the incident probe beam 20, and the second lens of power is tilted an angle δ from parallel with the first lens and the axis of tilt can rotate to a presettable radial angle C from the vertical. The effective lens parameters of such an assembly is given by the following expressions:

Spherical Power=S+U(1+½ sin² δ)

Cylindrical Power=U tan² δ. (10)

The principal meridians of the assembly's cylinder equivalent is aligned in the direction of the axis about which δ is produced. From a measurement standpoint, the optical assembly or any unknown optical components on a windscreen 14 presents the optical equivalent of a spherical lens of value A combined with a cylindrical lens of value B aligned along some axis with angle C from the vertical.

A well known characteristic of cylindrical lenses is that the effective lens power varies as the sine squared of the angle from the cylinder axis. Thus there are two cycles of variation in a complete rotation of the lens. Expressed analytically, if Ψ is the angle the shearing plane makes from the vertical, then the analyzer system will detect a lens power having the functional dependance F(Ψ) where $$F(\Psi) = A + B \sin^2 (\Psi + C). \quad (11)$$

The lens measurements of a given test point of any component can be fit to the above expression thus affecting the analysis. A more efficient computational procedure is derived by making the following equalities:

$$\alpha = -(\tfrac{1}{2})B \cos 2C$$

$$\beta = (\tfrac{1}{2})B \sin 2C$$

$$\mu = A + B/2$$

$$x = 2\Psi. \quad (12)$$

Equation (11) then becomes $$F(X/2) = \mu + \alpha \cos x - \beta \sin x. \quad (13)$$

Using orthogonality and expanding in sines and cosines series terms the α, β, and μ parameters are given by $$\alpha = \frac{2}{N} \sum_{j=1}^{N} F_j \cos\left(\frac{360}{2N} j\right)$$

$$\beta = \frac{2}{N} \sum_{j=1}^{N} F_j \sin\left(\frac{360}{2N} j\right)$$

$$\mu = \frac{2}{N} \sum_{j=1}^{N} F_j, \quad (14)$$

where N is the number of samples taken in a 360° rotation of the shearing plane, satisfying 360/2N=integer, and the $F_j$ are the respective lens power measurements taken at the angles 360/2N, 2(360/2N), 3(360/2N), etc. The resultant effective lens components are calculated back from the relations of equation (12), i.e.

$$A = \mu + \sqrt{\alpha^2 + \beta^2} \quad (15)$$

$$B = (-)\overset{2}{\sqrt{\alpha^2 + \beta^2}}$$

$$C = (-\tfrac{1}{2}) \tan^{-1}\left(\frac{\alpha}{\beta}\right) + \phi^1$$

The (−) sign in B is chosen for negative cylinder form and $\phi^1 = \Delta\Psi - \Psi_o$ where ΔΨ=360/2N and $\Psi_o$ is the initial sampling angle shift.

Figure 9:
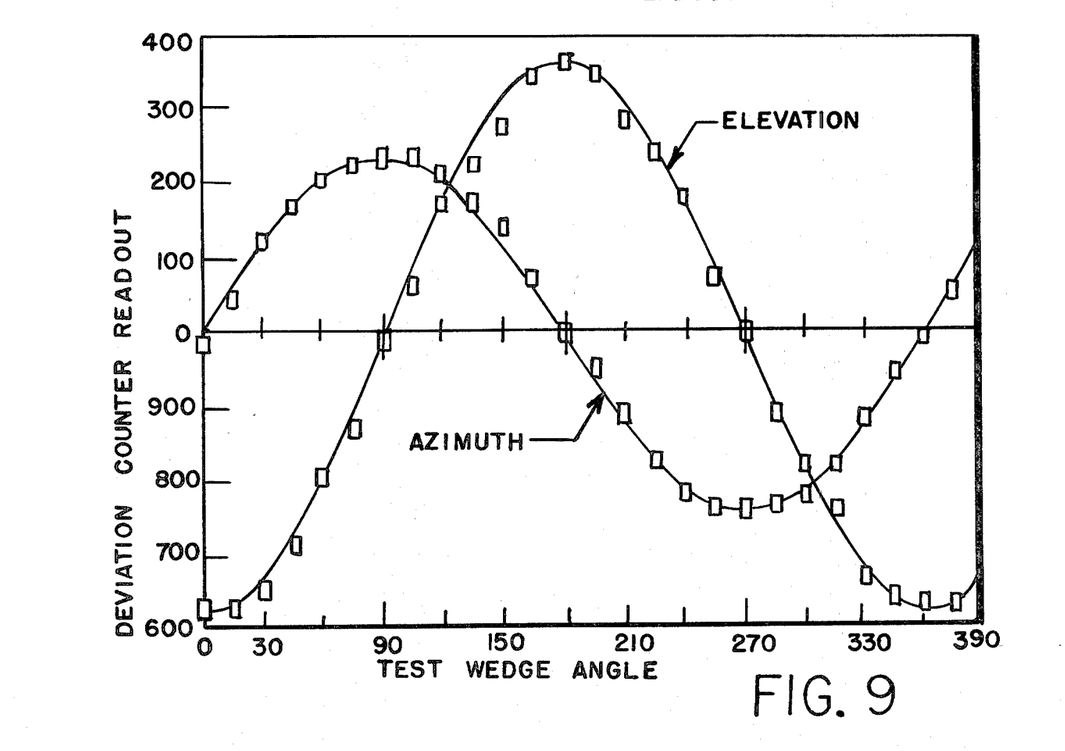
FIG. 9 is a graphic representation of an example of prismatic deviation calibration curves.

The calibration and measurement of the prismatic deviation responsivity is done by recording the cumulative deviation correcting stepping motor step signals as presented on data bus 152. The direction signal is used to select incrementation or decrementation of the counters 160 and 162 depending on the direction. A pair of azimuth-elevation prismatic deviation calibration curves are obtained by rotating a 0.50 prism diopter wedge through angle β in the test region. The results of this test are shown in FIG. 9. The calibration data is very accurately fit by sinusoidal functions, i.e. azimuth=238 sin β and elevation=−364 cos β. From the chi-squared parameter of these curves the precision is shown to be 0.01°.

Figure 10:
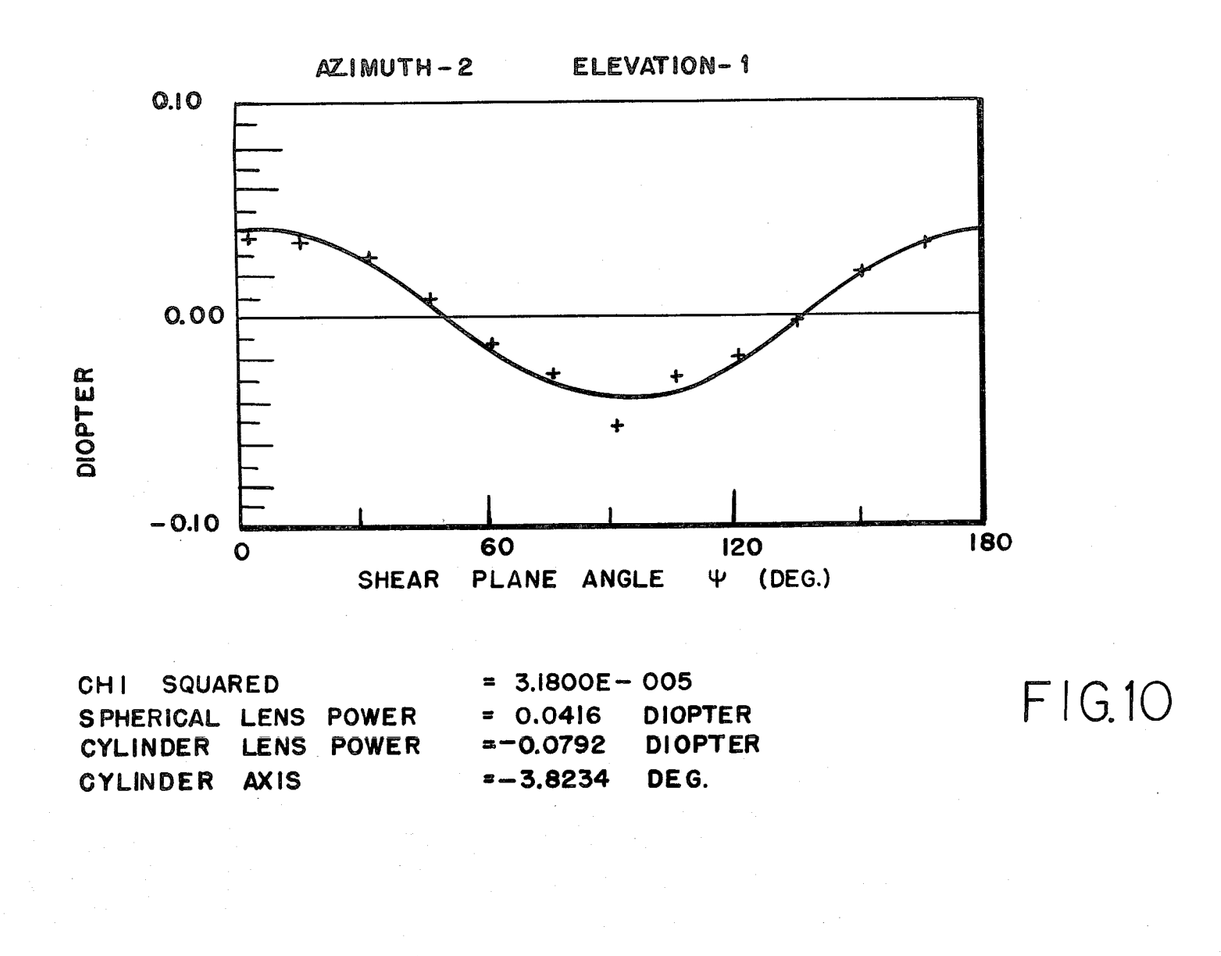
FIG. 10 is a graphic representation of a typical data curve obtained for an F-111 windscreen transparency.

With the computations on windscreen 14 at each test point 25 conducted as above in conjunction with the prismatic measurement, the optical quality of the windscreen 14 is completely characterized. An example of the measurement of a given test point 25 on an F-111 windscreen 14 is shown in FIG. 10. Extremely fine resolution is obtained of the weak lens component making up the optical quality at the test point in question.

The lens power map of windscreen 14 renders a comprehensive ophthalmic model that can be taken into account for the manufacturing of pilot spectacles that compensate for the windscreen, or used for the reforming or reconstruction of the windscreen. Most importantly, this map of lens parameters can be used to quantify the selection criteria for acceptable aircraft windscreens. Any of several numerical criterions can be invoked for this decision making process. For example, the maximum less excursion multiplied by the prismatic error may be used as the selection parameter. A map of this parameter versus windscreen angular position coordinates can be made. A numerical inspection for quality can then be made from this map. There are other formats for the presentation of the lens parameter data obtained from the windscreen which certainly heretofore have not been possible prior to this invention.

Although this invention has been described with reference to a particular embodiment, it will be understood to those skilled in the art that this invention is also capable of further and other embodiments within the spirit and scope of the appended claims.

I claim:

1. An optical distortion analyzer system for automatically quantifying the optical quality of a transparency comprising:
   (a) means for supporting said transparency;
   (b) means operably connected to said transparency supporting means for moving said supporting means and therefore said transparency about a vertical axis and a horizontal axis;
   (c) means for providing a probe beam of electromagnetic radiation in optical alignment with said transparency, said probe beam having a predetermined angular orientation in a predetermined direction and position in space, said probe beam passing through said transparency as said transparency is moved about said vertical and horizontal axes thereby establishing a plurality of test points at the intersection of said probe beam with said transparency;
   (d) means optically aligned with said probe beam for receiving and analyzing said probe beam after having passed through said transparency, said probe beam having said predetermined angular orientation and predetermined direction and position in space altered as it passes through said transparency, wherein said analyzer means includes means for determining horizontal and vertical prismatic deviations of said transparency at said test points as said probe beam passes therethrough and providing signals indicative thereof and means for determining the cylindrical lens power component, spherical lens power component and principal meridian angle of said transparency at said test points and providing signals indicative thereof, said means for determining said cylindrical lens power component and said principal meridian angle includes a photo diode array system in optical alignment with said probe beam after being passed through said transparency and means in optical alignment with said probe beam and positioned between said transparency and said photo diode array system for rotating the image axis of said probe beam after passing through said transparency;
   (e) means in optical alignment with said probe beam and positioned between said image axis rotation means and said photo diode array system for eliminating lens power error resulting from the displacement of said test points along said probe beam axis; and
   (f) means for processing said signals indicative of prismatic deviations, lens power components and meridian angle and correlating said prismatic deviations, lens power components and meridian angle with said plurality of test points on said transparency.

2. An optical distortion analyzer system as defined in claim 1 wherein said lens power error eliminating means comprises a dual channel differential shearing interferometer, said dual channel differential shearing interferometer including means optically aligned with said image axis rotation means for receiving said probe beam and directing said probe beam into two separate beam paths; a bias lens, a shearing plate, a back correcting lens and a sequencing shutter being positioned within each of said beam paths; and means for receiving said pair of beam paths after passing through said bias lenses, shearing plates, back correcting lenses and sequencing shutters, respectively, and focusing said two beam paths onto said photo diode array system.

3. An optical distortion analyzer system as defined in claim 2 further comprising means in optical alignment with said probe beam and positioned adjacent said photo diode array system for compensating for transmissivity variations which take place at said of test points on said transparency.

4. An optical distortion analyzer system as defined in claim 3 wherein said transmissivity compensating means comprises a variable density filter wheel in operable relationship with said photo diode array system and positioned such that said probe beam passes through said filter wheel before reaching said photo diode array system.

5. An optical distortion analyzer system as defined in claim 4 wherein said means for determining said principal meridian angle further comprises means for restoring said probe beam to a position parallel and superimposed with said predetermined direction and position in space.

6. An optical distortion analyzer system as defined in claim 5 wherein said means for determining said principal meridian angle further comprises means for compensating for the effect of multiple reflections that occur at said plurality of test points as said probe beam passes through said transparency.

7. An optical distortion analyzer system as defined in claim 6 wherein said means for compensating for the effect of multiple reflections comprises a pinhole aperture plate operably associated with said probe beam direction and position restoring means.

8. An optical distortion analyzer system as defined in claim 7 wherein said means for determining said horizontal and vertical prismatic deviations comprises means for receiving said probe beam after passing through said transparency, means for comparing said predetermined angular orientation of said probe beam with said altered angular orientation and producing said signals indicative of prismatic deviations, and means for utilizing said signals indicative of prismatic deviations for restoring said probe beam to its predetermined angular orientation.

9. An optical distortion analyzer system as defined in claim 8 wherein said means for providing said probe beam is a laser.

* * * * *